(12) United States Patent
Craig (10) Patent No.: US 7,113,277 B2
(45) Date of Patent: Sep. 26, 2006

(54) SYSTEM AND METHOD OF AEROSOLIZED AGENT CAPTURE AND DETECTION

(75) Inventor: William C. Craig, Endwell, NY (US)

(73) Assignee: Lockheed Martin Corporation, Bethesda, MD (US)

( * ) Notice: Subject to any disclaimer, the term of this patent is extended or adjusted under 35 U.S.C. 154(b) by 347 days.

(21) Appl. No.: 10/437,962

(22) Filed: May 14, 2003

(65) Prior Publication Data

US 2004/0227938 A1 Nov. 18, 2004

(51) Int. Cl.
 G01J 3/30 (2006.01)
 G01N 21/00 (2006.01)
 B32B 27/04 (2006.01)
 B32B 27/12 (2006.01)

(52) U.S. Cl. ............... 356/318; 73/23.2; 73/28.04; 73/865.5; 356/317; 356/335

(58) Field of Classification Search ............... 356/317, 356/318, 319, 336–343; 73/23.2, 28.04, 73/865.4; 422/83, 99, 186; 436/104, 164
See application file for complete search history.

(56) References Cited

U.S. PATENT DOCUMENTS

| | | | |
|---|---|---|---|
| 2,076,554 A | 4/1937 | Drinker et al. ............... 88/14 |
| 3,088,364 A | 5/1963 | Rozsa et al. .................. 88/14 |
| 3,554,005 A | 1/1971 | Koblin et al. .................. 73/28 |
| 3,654,801 A | 4/1972 | Keefer et al. .................. 73/28 |
| 3,868,222 A | 2/1975 | Barringer ............... 23/230 EP |
| 3,970,428 A | 7/1976 | Barringer ............... 23/230 EP |
| 3,985,619 A | 10/1976 | Barringer ............. 195/103.5 R |
| 4,056,969 A | 11/1977 | Barringer ........................ 73/28 |
| 4,192,176 A | 3/1980 | Barringer ........................ 73/28 |
| 4,220,414 A | 9/1980 | Barringer .................... 356/318 |
| 4,415,265 A | 11/1983 | Campillo et al. ........... 356/338 |
| 4,468,468 A | 8/1984 | Benninghoven et al. .... 436/173 |
| 4,598,577 A | 7/1986 | Jowitt et al. .................... 73/23 |
| 4,652,128 A | 3/1987 | Tsunoyama et al. ........ 356/318 |
| 4,801,209 A | 1/1989 | Wadlow ..................... 356/417 |
| 4,986,658 A | 1/1991 | Kim ........................... 356/318 |
| 5,109,691 A | 5/1992 | Corrigan et al. ........... 73/23.36 |
| 5,345,809 A | 9/1994 | Corrigan et al. ............. 73/23.2 |
| 5,379,103 A | 1/1995 | Zigler ........................... 356/73 |
| 5,425,263 A | 6/1995 | Davies et al. .............. 73/28.05 |
| 5,446,538 A | 8/1995 | Noll ........................... 356/318 |
| 5,585,575 A | 12/1996 | Corrigan et al. ......... 73/863.71 |
| 5,627,641 A | 5/1997 | Mauchien et al. .......... 356/318 |
| 5,715,053 A | 2/1998 | Loge ........................... 350/318 |
| 5,798,832 A | 8/1998 | Hnilica et al. ............. 356/316 |
| 5,847,825 A | 12/1998 | Alexander .................. 356/318 |
| 5,880,830 A | 3/1999 | Schechter ................... 356/318 |
| 5,912,466 A | 6/1999 | Funsten et al. ............. 250/372 |
| 5,991,020 A | 11/1999 | Loge ........................... 356/316 |
| 6,008,896 A | 12/1999 | Sabsabi et al. ............. 356/318 |
| 6,034,768 A | 3/2000 | Fraser et al. ................ 356/316 |

(Continued)

Primary Examiner—Layla G. Lauchman
(74) Attorney, Agent, or Firm—Burns & Levinson LLP; Jacob N. Erlich; John Hamilton (57) ABSTRACT

System and method of aerosolized agent detection. Multi-part collection tape is employed for capturing particles of interest for immediate analysis and optional forensic preservation and recording information related to capture and subsequent real-time analysis. Laser induced breakdown spectroscopic processing is employed and spectra attributable to known collection tape materials is subtracted to derive particle spectra for comparison to known hazardous agent spectra.

23 Claims, 5 Drawing Sheets

U.S. PATENT DOCUMENTS

| | | |
|---|---|---|
| 6,259,101 B1 | 7/2001 | Wexler et al. ............ 250/423 P |
| 6,359,687 B1 | 3/2002 | Cheng ........................ 356/318 |
| 6,806,465 B1 * | 10/2004 | Anderson et al. ........... 250/287 |
| 6,847,446 B1 * | 1/2005 | Shilling ...................... 356/318 |
| 6,887,710 B1 * | 5/2005 | Call et al. ..................... 436/53 |
| 2002/0003210 A1 | 1/2002 | Marcus ....................... 250/288 |
| 2004/0028561 A1 * | 2/2004 | Daugherty et al. ........... 422/99 |

* cited by examiner

SYSTEM AND METHOD OF AEROSOLIZED AGENT CAPTURE AND DETECTION

BACKGROUND OF THE INVENTION

The present invention relates generally to the capture and detection of aerosolized agents, such as, for example, chemical or biological biowarfare agents, and, more particularly to systems for and methods of continuous sampling and analysis of aerosol samples potentially containing such agents.

As the anthrax mailings of October of 2001 demonstrated, a number of vectors are available to the terrorist bent on social disruption. Biological warfare agents have long been a domestic terror concern and the use of the mails as a delivery method has many serious consequences. Not only are mail recipients at risk, but all those who handle or are in the vicinity of the mail piece during processing are at risk as well. In the extreme case, a few strategically posted items could bring a nation's postal administration, such as the United States Postal Service, to a complete halt. If mail delivery were to cease, even for a few days, the impact to trade, commerce, finance and general communication is incalculable.

Thus, it is desirable to capture and identify aerosolized particulate matter that may issue from sources requiring monitoring. Such sources could include mail pieces being sorted or otherwise processed, building ventilation systems, import and export cargo and military point detection systems.

Prior attempts to detect and identify pathogens in the mail use chemical or bio fluorescence methods. An example of a chemical method is Polymerase Chain Reaction (PCR). PCR is a DNA amplification technique that has been used successfully in laboratory environments in recent years. PCR is a powerful and useful technique but it does not generate results in real-time. The fastest PCR systems require a minimum of 30–60 minutes to process a sample and render a result. This time lag is problematic, as the mail piece containing the hazard will have traveled further down stream potentially affecting postal workers or postal customers. Other techniques using multi spectral ultra-violet (UV) fluorescence techniques may render a result quickly, but are prone to false alarms and are often non-specific relative to the threat. For example, non-threatening biological particulate in the right size range will typically cause a UV sensor system to indicate a false positive detection. Also, even if hazardous particles are correctly detected, UV based sensors will typically indicate the presence of the threat without specifically identifying the agent.

SUMMARY OF THE INVENTION

The present invention describes systems for and methods of capturing and rapidly identifying aerosolized particulate matter in fluid samples to be analyzed, such as, for example, hazardous agents issued from mail pieces during sorting and other processing steps. The invention is applicable to a range of uses outside of the mailing industry, including building ventilation systems, checking import and export cargo by customs officials and military point detection systems. The system provides this timely notification without the possible false alarms inherent in many of the systems described above.

The present invention provides a sample capture tape and an aerosolized agent detector employing the tape, the detector including a dispenser having a fluid sample input port and an exit port for providing a concentrated particle stream, an analyzer providing real-time detection of aerosolized agents, and a means for advancing a section of the tape from the vicinity of the dispenser exit port to the analyzer. The sample capture tape includes a data storage portion, and the tape is oriented and configured to receive the particle stream from the dispenser exit port and collect selected particles on one or more collecting portions. An encoder stores information relative to the fluid samples' collection and analysis on the data storage portion.

The one or more sample collection portions of the capture tape further comprises an immediate analysis portion and an optional sample preservation portion. A wide variety of alternate approaches are available in capturing the desired particles. For example, the sample collection portions may be comprised of permeable filter, adhesive-coated or electrically charged materials, or may be comprised of a material with a surface incorporating microscopic features designed to capture particles impinged thereupon. Other capturing mechanisms will be readily apparent to artisans and are deemed to be within the scope of the present invention.

The particle stream exiting the dispenser preferably, though not exclusively, impinges nearly perpendicularly on the sample collection portions of the sample collection tape. In one preferred embodiment, the dispenser further comprises a virtual impactor for pre-concentrating the particle stream. As will be described in detail below, various configurations are allowed for in which the particle stream impinges from either side of the sample capture tape.

In certain embodiments, the means for advancing the sample capture tape comprises a reel-to-reel like system, wherein the sample capture tape is provided on a source reel and a take-up reel pulls the tape at the desired rate, or in indexed intervals, through the path of the particle stream. The collection process can, thus, continue in an uninterrupted fashion even as the sample capture tape is in the process of advancing. A sterile tape reel may additionally be employed to interleave a sterile enclosing layer between the sample collection tape layers on the take-up reel.

The analyzer, in preferred embodiments, is comprised of a laser-induced breakdown spectroscopic (LIBS) system adapted to differentiate between spectra elements attributable to portions of vaporized sample capture tape and spectra elements attributable to various potentially hazardous agent particles.

The present invention provides a method of continuous detection of aerosolized agents comprising the steps of: providing a source of sample capture tape comprised of at least a first collection portion and a data storage portion; collecting particles by impinging a particle-laden aerosol stream on the first collection portion; advancing the first collection portion from the particle stream to an analyzer; analyzing in real-time the particles collected on the first collection portion; and electronically encoding information on the data storage portion related to the sample collection and analysis. The method efficiency is enhanced by optionally pre-concentrating the fluid to be analyzed to form the particle-laden aerosol stream. The advancement of the sample capture tape allows the collection process to continue in an uninterrupted fashion, and synchronization between collection and analysis allows continuous detection.

The method may further include the step of collecting samples from the particle-laden stream on a second collection portion of the sample capture tape at a time nearly simultaneous with the sample collecting on the first portion, and preserving the samples collected on the second collection portion. The preservation may be effected by covering the particles collected on the second collection portion with a sterile tape, such as an interleaving reel-to-reel configuration as described in more detail below.

DETAILED DESCRIPTION OF THE INVENTION

Certain preferred embodiments of the present invention will now be described with reference to the figures identified above.

Figure 1:
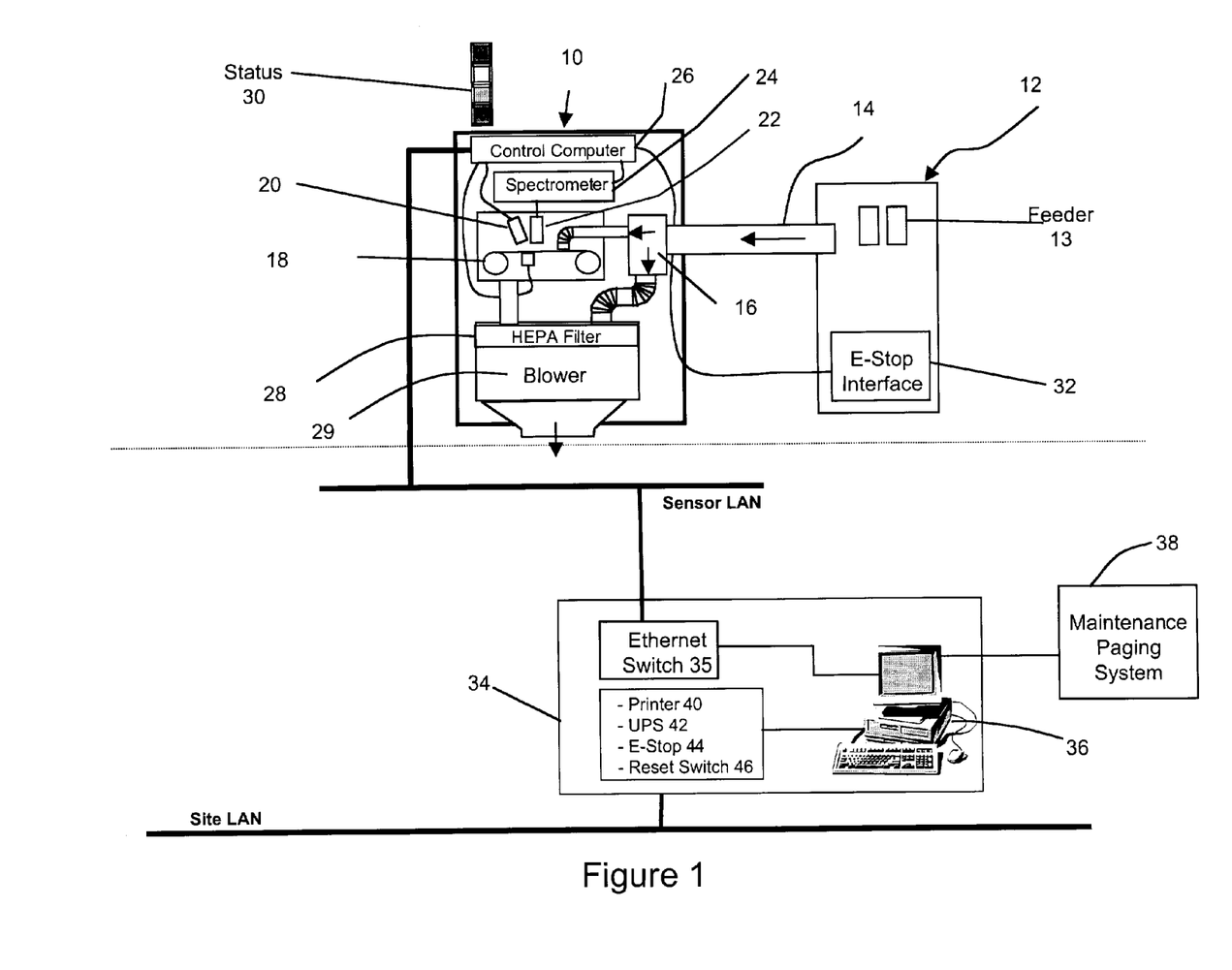
FIG. 1 is diagrammatic view of a an aerosolized agent detecting system configured for use with mail processing equipment.

The present invention is now described more fully. For the purpose of illustration only, the present invention is described in embodiments configured for use in a mail testing system. As discussed above, the aerosol agent detection system and method are useful in a variety of testing and/or monitoring environments. Referring to FIG. 1, a mail testing system 10 is attached to a conventional piece of mail processing equipment, 12. In order to transport and sort a mail piece, the processing equipment 12 typically pinches an envelope tightly between two flat transport belts (not shown) moving at high speed. An induction point into the mail processor is called a feeder 13, and at this point an envelope is first pinched between the transport belts. As the envelope is pinched, air is forced from the envelope and with it any particulate matter contained therein. Aerosol collection sample tube 14, which is under vacuum, captures air forced from the envelope. A virtual impactor 16 dispenses a pre-concentrated particle stream by separating smaller aerosolized particles from larger ones contained in the air delivered through collection tube 14.

The smaller particles of interest are then impinged on a collection tape 18, which captures a sufficient number of them to perform testing and, in certain preferred embodiments, sample preservation. After a predefined collection period, collection tape 18 is indexed to an adjacent location in order that a new sample of the air stream may be impinged upon a fresh portion of the collection tape. A Laser Induced Breakdown Spectroscopy (LIBS) method is used to analyze the particles collected on collection tape 18.

The LIBS process requires that the particulate matter collected on the tape 18 be vaporized using a high-energy laser 20. The electromagnetic spectrum radiated as a result of the vaporization of the collected particles and the portion of tape 18 upon which they are collected is captured by optics 22 and transmitted to a spectrometer 24, such as the Ocean Optics LIBS2000+ Broad Band Spectrometer. Spectrometer 24 interprets the relative intensity of the radiation at all frequencies in the band of interest—typically 200–980 nm and generates a spectral curve. The spectral curve is then sent to control computer 26 for analysis. In order to protect personnel in the vicinity of system 10, collected air is exhausted through a High Efficiency Particle Arresting (HEPA) filter 28 under the impetus of blower 29. Control computer 26 compares the spectral curve to a library of spectral curves for known biohazards and typical hoax or naturally occurring powders. Control computer 26 may also subtract from the spectral curve spectral elements known to be attributable to the portion of vaporized tape 18.

If the control computer 26 detects a high likelihood of a biohazard event, a visual, audio and/or process control indication of the detection is provided. In the system depicted, event detection is indicated by turning a status light 30 on and invoking an E-Stop interface 32 for cessation of mail processing. If multiple systems are implemented in a single building, a central control system 34 may provide overall supervisory control and monitoring functions for all systems. In the embodiment depicted, central control system 34 is comprised of an Ethernet interface 35, a control computer 36, various peripherals including a printer 40, uninterruptible power supply (UPS) 42, an E-Stop switch 44, and a reset switch 46. A maintenance paging system 38 can also be integrated to alert site personnel if a bio detection event has occurred or if maintenance action is required.

Figure 2:
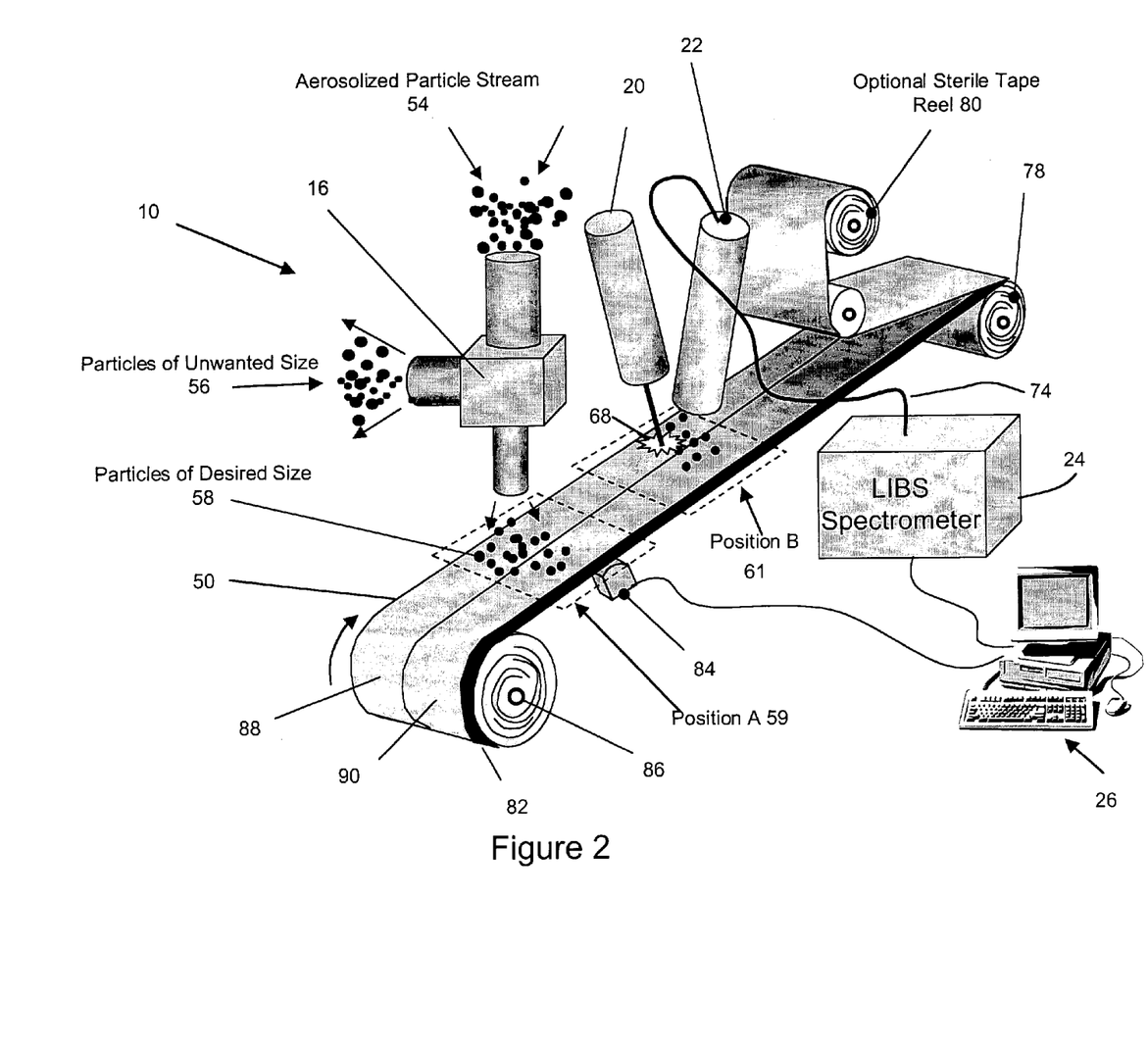
FIG. 2 is an isometric schematic diagram of an aerosolized agent detecting system employing an optional sterile tape.

A more detailed view of testing system 10 can be seen in FIG. 2.

A specifically designed collection tape 50 is arranged in a reel-to-reel configuration as shown with a source reel 86 and a take-up reel 78. Collection tape 50, as will be described in further detail below, is comprised of at least a first collection section 88 for particle collection for immediate analysis and a data encoding region 82, but preferably further comprises a second collection section 90. The two collection sections 88,90 of the particular configuration of system 10 depicted are used for particulate collection; one is designated the LIBS collection section 88 and is used for analysis of the particulate deposited thereon, and the other forensic section 90 for preserving part of the collected particle sample for forensic purposes. Encoding region 82 of tape 50 may be comprised of any number of mechanical and/or electrical encoding media, but is shown here as a magnetic strip for data storage along an edge of the tape.

Virtual impactor 16 receives an aerosolized particle stream 54, separates unwanted particles 56 based on particle size, and dispenses an aerosolized stream laden with particles of interest 58. The use of virtual impactor 16 raises the efficiency of testing system 10, but it is not necessary to all embodiments of the present invention. Any dispenser capable of delivering a particle stream derived from a fluid sample is suitable for use. Referring again to FIG. 2, the particles of interest 58 are impinged on collection tape 50 while at Position A 59.

After a predetermined collection period, the section of collection tape impinged upon is indexed to Position B 61. A portion of the particles 58 at Position B is then vaporized using laser 20. The resulting spectral emission is captured by the optics 22, which focus the emitted light for transmission to the spectrometer 24 through a fiber optic link 74. After the spectral characteristics are quantified by the spectrometer, spectral data is then sent to control computer 26 for analysis. Control computer 26 employs pattern-matching techniques to identify the particulate matter impinged and collected on collection tape 50.

The invention also includes a means for advancing or indexing the tape relative to the impinging particle stream, laser 20 and optics 22. Although a number of mechanisms could be employed, the advancing means is depicted as a reel-to-reel configuration. As the tape is indexed, it is stored on the take-up reel 78. To prevent particles from being transferred between tape layers on take-up reel 78, a sterile tape 80 is wound between the layers of collection tape. This creates a closed environment for effectively preserving any particles captured on the tape. After processing the spectral information, and as the tape is indexed, control computer 26 writes parametric information on the magnetic strip comprising the encoding region 82 in this embodiment, which is situated along the edge of the collection tape, using magnetic write head 84. The magnetic write head 84 is illustrated as positioned between the impinging stream and the detection optics, but alternatively could be located further along the trajectory of the tape, or may even be comprised of multiple write heads. The type of data that may be encoded may include information related to the source of aerosolized particle stream 54, time/date of collection, identity and/or location of equipment employed in capture and analysis, and the results of analysis, such as the spectral information captured, results of the pattern matching analysis, etc.

Figure 3A:
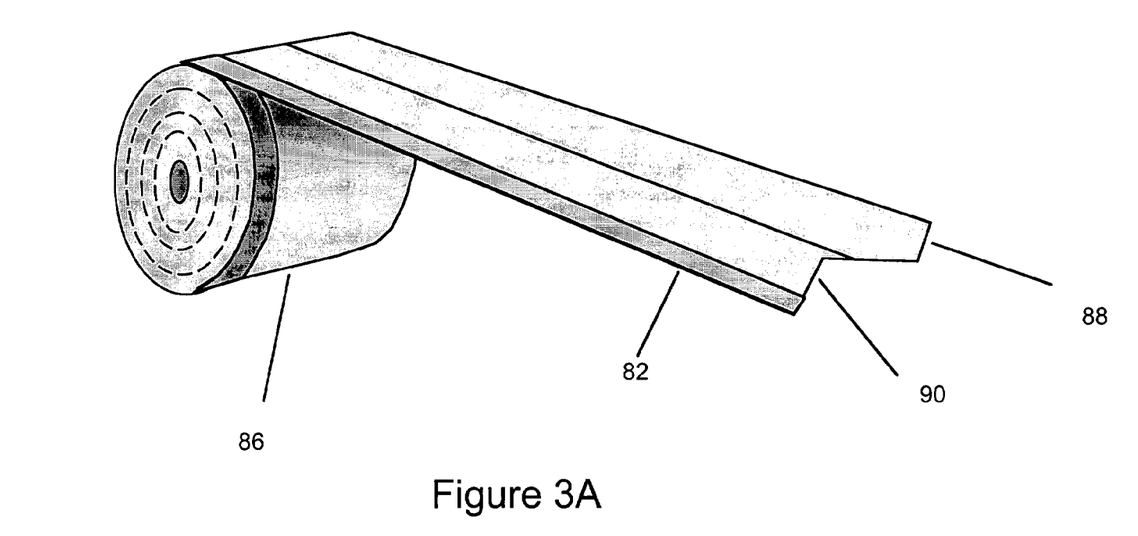
FIG. 3A is an isometric view of sample capture tape in roll form depicting multiple portions thereof.
Figure 3B:
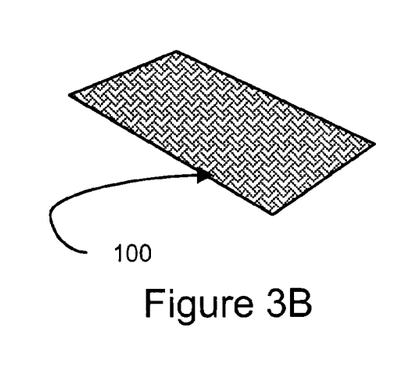
FIGS. 3B–D are diagrammatic views of various embodiments of materials usable as collection portions of the sample capture tape.
Figure 3C:
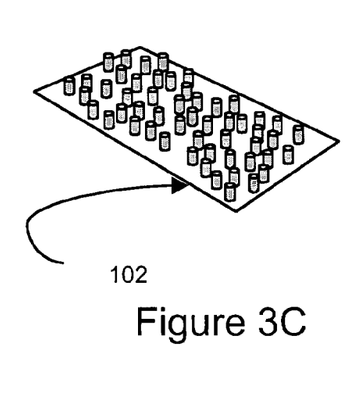
Figure 3D:
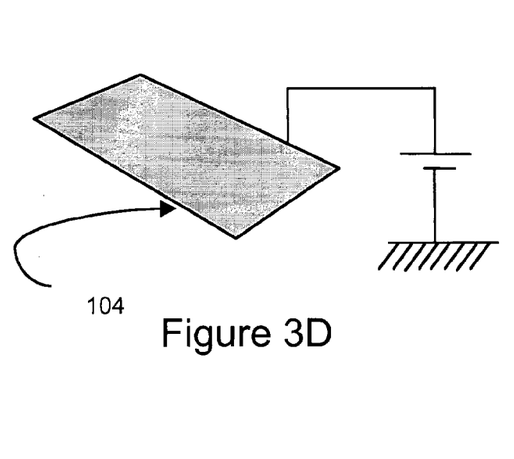

The collection tape 50, as shown in FIG. 3A as supplied on a source reel 86, is comprised of three distinct sections; the encoding region 82 (e.g., magnetic edge), the LIBS collection section 88, and the forensic section 90. The magnetic embodiment of encoding region 82 is designed to store digital information about when and where the LIBS analysis was done, and the results of the analysis. Any other storage media (e.g., optical, mechanical, etc.) suitable for quick recording of information can be suitably employed in the encoding region. The LIBS and forensic sections of the tape are specifically designed to capture the aerosolized particles impinged thereon. A number of design alternatives are suitable for use as the collection sections 88,90. FIG. 3B illustrates an embodiment of a collection tape 100 comprised of a porous filter type material designed to trap particles as the air passes through the material. The tape 100 may have an adhesive coating designed to stick to the particles impinged on its surface. FIG. 3C illustrates an embodiment of a collection tape 102 having a surface engineered with microscopic hooks or protrusions that will tend to trap particles. As another alternative, FIG. 3D shows a collection tape 104 having a charged surface that attracts particles of interest that have passed through an electrostatic field imparting the opposite charge to them. As stated above, forensic section 90 allows material to be retained for confirmation testing using alternative methods and for legal evidence.

Referring again to FIG. 2, regardless of how the particles are captured, the LIBS collection section 88 is reserved for LIBS processing, which requires the particles in the section 88 be vaporized by the high-energy laser 20. The resulting spectra are captured for analysis. Control computer 26 performs the analysis, subtracting the known spectral characteristics of the collection tape from the spectral information captured. This is done to isolate the signal of the particulate from that of the tape substrate.

Figure 4:
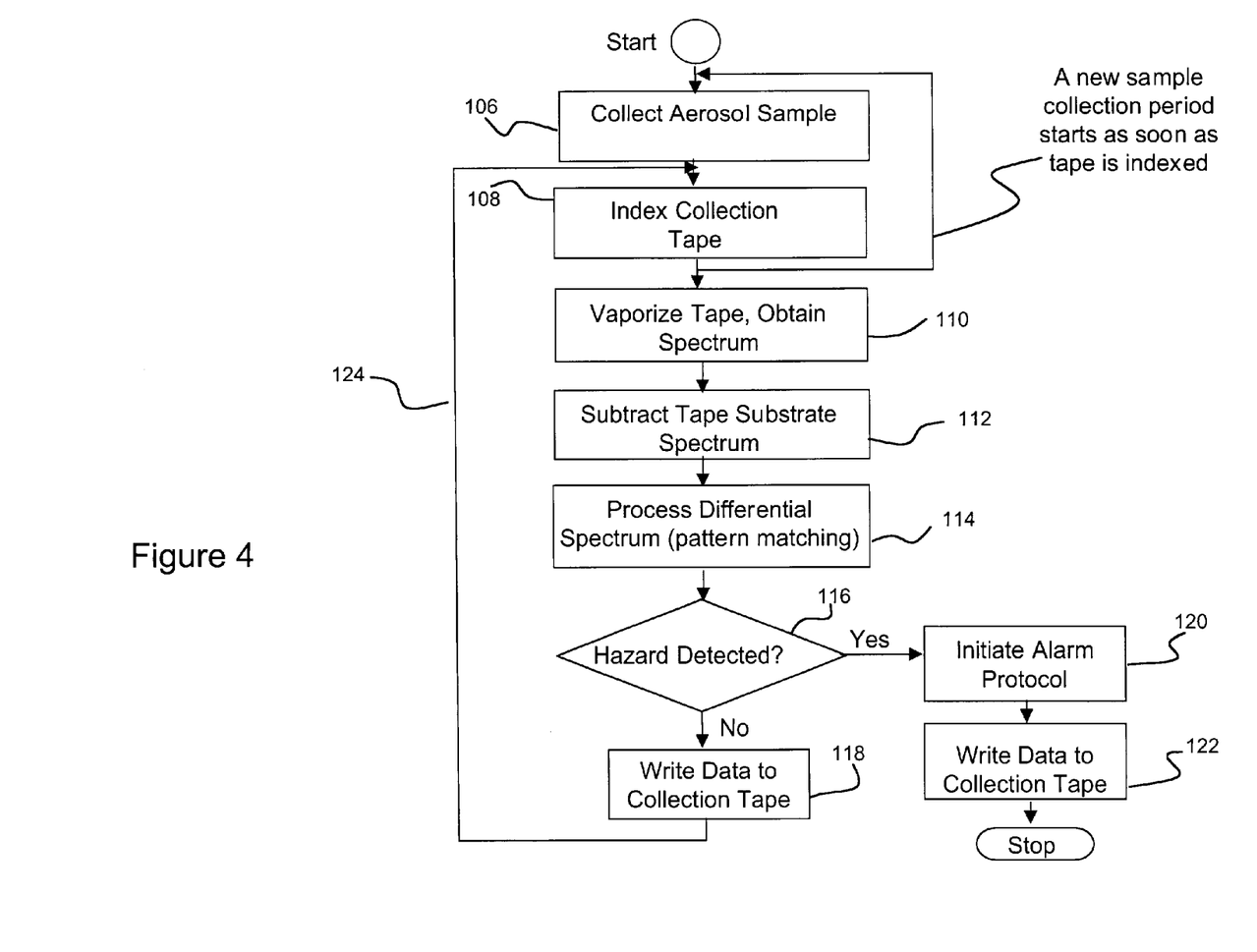
FIG. 4 is a flow diagram of the operational functions of an embodiment of the present invention.

A flow chart illustrating a preferred method of using system 10 is shown in FIG. 4. The first step is the particulate collection process 106. The length of time required for the collection is a programmable parameter, which will depend on several factors related to the application of the invention, including the background particulate loading, the expected duration of a bio-release event, and the expected biohazard particulate concentration of the event in terms of agent containing particles per liter of air (ACPLA). For a postal application, the expected release will have high ACPLA count over a very short duration. The dwell time for the postal application is therefore short, on the order of 1 to 10 minutes. For open-air environment point detection applications, where much lower ACPLA is expected, the dwell time may be 30–90 minutes or more.

In step 108, after collecting particulate for the specified dwell time, the tape is indexed. When the tape is indexed, a fresh section of the tape is moved into position for particulate collection. Also, as the tape is indexed, the portion of the tape most recently exposed to the aerosolized particle stream for the programmed dwell time is moved into position for LIBS analysis. In step 110, LIBS processing requires that a portion of the collection tape be exposed to a high-energy laser, for example the ULTRA CFR Nd:YAG laser from Big Sky Laser Technologies. When the laser is activated, the high-temperature of the laser focused on the LIBS portion of the collection tape creates plasma. As the plasma cools, the excited atoms in the plasma emit light at wavelengths characteristic of the elements contained in the particulate sample on the tape, as well as the elemental constituents of the tape itself. Since the tape is a known quantity previously characterized using the LIBS process, the spectral elements of the tape can be algorithmically subtracted, in step 112, from the captured plasma spectrum.

In step 114, the resulting differential spectrum is then used for the signal processing and pattern matching process. The pattern matching process first resolves the captured differential spectrum into a set of characteristic features. These features are then compared to a library of feature sets for known biohazards previously characterized using the LIBS process and a similar apparatus. Several established methods exist for the pattern-matching algorithm including neural network and least sum of squares techniques. The output of the pattern matching process is a set of probabilities for each of the library substances the captured spectrum is tested against. In step 116, the probabilities are compared to one or more predefined thresholds for a determination whether a hazardous agent has been detected.

If any of the probabilities exceed the one or more predefined thresholds, an alarm condition exists. If an alarm condition exists, an alarm protocol is initiated in step 120. The protocol will be defined by the user of the technology, but will typically include shutting down any associated equipment, activating appropriate audio/visual alarms and initiating events such as paging key personnel and notifying the appropriate first responder agency. The method of communication can be via e-mail, telephone messages, pager messages, or a combination, based on the user's preference. All information relative to the bio-detection event is recorded on the encoding region 82 of the collection tape 50. If, after processing the differential spectrum, an alarm condition does not exist, the results of the spectrum analysis are still encoded on the encoding region of the tape, and the process begins again as determined by the programmed collection interval.

Figure 5:
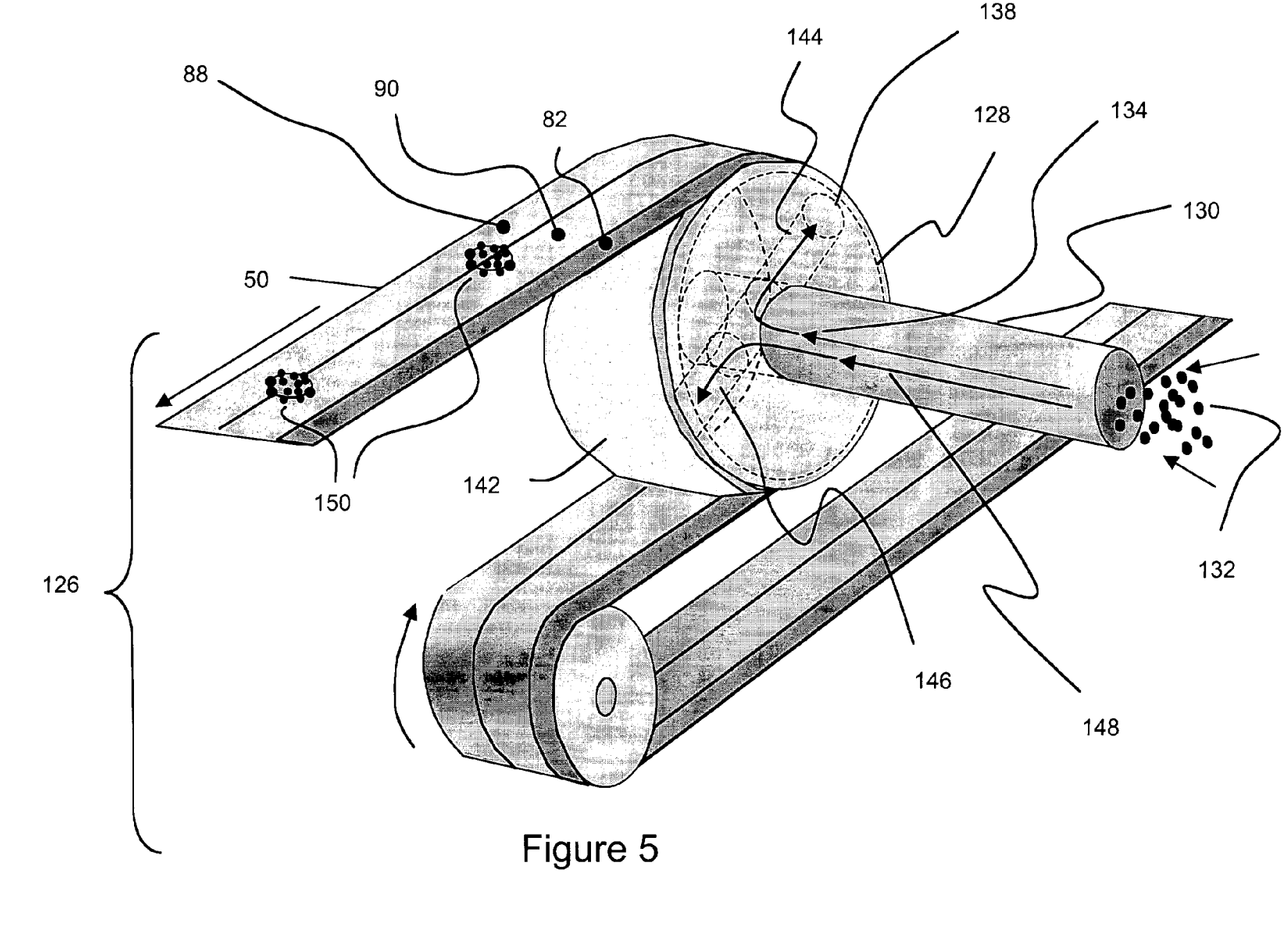
FIG. 5 is an isometric schematic diagram of an alternate collection mechanism designed for continuous collection to eliminate the possibility that an event might be lost during the collection process.

In another embodiment of the invention, the collection process occurs in a continuous fashion, without any interruptions that might be introduced in indexer-based configurations. Referring to FIG. 5, a continuous collection device 126 is comprised of a rotating pulley 128 on a hollow shaft 130. A particle-containing air stream 132 enters through the hollow shaft 130. For a half of the rotation of pulley 128, air stream 132 follows path 134 through outlet port 144 to impinging point 138. For the other 180 degrees of rotation, port 144 is effectively closed as a result of its adjacency to sealing surface 142. During this interval, port 146, which is 180 degrees out of phase with port 144, is simultaneously open and air stream 132 will follow path 148 to impinge upon a different portion of collection tape 50. This mechanism allows sample collection to be performed in a continuous fashion, eliminating the possibility of missing a very short duration release as the tape is indexed. Collected particulate 150 are then processed as described in proceeding paragraphs. Depending on the design of the ports incorporated into the pulley 128, air stream 132 can be either draw through the collection tape if the tape is made from a porous material mesh, such as depicted in FIG. 3B, or it can be impinged against collection tapes comprised of solid materials with particle-arresting surface features, such as shown in FIGS. 3C and 3D.

Although the invention has been described with respect to various embodiments, it should be realized this invention is also capable of a wide variety of further and other embodiments within the spirit and scope of the appended claims.

I claim:

1. An aerosolized agent detector, comprising:
a sample dispenser providing a concentrated particle stream, said sample dispenser having a sample input port configured and disposed to receive fluid samples and an exit port to deliver said particle stream derived from said fluid samples;
a section of capture tape oriented to receive said particle stream from the exit port and collect selected particles on one or more laser vaporizable sample collection portions thereof, said capture tape including a data storage portion;
a laser induced breakdown spectroscopic analyzer providing real-time detection of aerosolized agents from among the collected particles, said analyzer including a laser capable of vaporizing at least one of the one or more laser vaporizable sample collection portions of said capture tape and a spectrometer adapted to obtain spectral elements attributable to vaporized sample collection portions of said capture tape and spectral elements attributable to said collected particles;
a processor for differentiating between the spectral elements attributable to said vaporized sample collection portions of said capture tape and spectral elements attributable to said collected particle;
a means for advancing the section of capture tape from the vicinity of said sample dispenser exit port to said analyzer; and
an encoder storing on the data storage portion information relative to the fluid samples collection and analysis.

2. The detector of claim 1, wherein the one or more sample collection portions further comprises a sample analysis portion and a sample preservation portion.

3. The detector of claim 2, further comprising a sterile tape dispenser for enclosing at least the sample preservation portion following sample collection.

4. The detector of claim 1, wherein the dispenser further comprises a virtual impactor.

5. The detector of claim 1, wherein the particle stream impinges nearly perpendicularly on the one or more sample collection portions.

6. The detector of claim 1, wherein the one or more sample collection portions are comprised of a porous filter material.

7. The detector of claim 1, wherein
the capture tape is provided on a source reel; and
the advancing means further comprises a take-up reel to receive the capture tape following analysis.

8. The detector of claim 7, further comprising a sterile tape reel oriented so as to interleave a sterile tape between layers of the capture tape on the take-up reel.

9. The detector of claim 1, wherein the advancing means advances the section of capture tape in timed intervals.

10. The detector of claim 1 wherein the advancing means allows the collection process to continue in an uninterrupted fashion even as the tape is in the act of advancing.

11. The detector of claim 1, wherein the fluid sample is comprised of an aerosol.

12. The detector of claim 1, further comprising an alarm for indicating detection of aerosolized agents.

13. A continuous aerosolized agent detection method, comprising the steps of:
providing a source of sample capture tape comprised of one or more laser vaporizable collection portions and a data storage portion;
collecting particle samples by impinging a particle-laden aerosol stream on the one or more laser vaporizable collection portions;
advancing the one or more collection portions from the aerosol stream to a laser induced breakdown spectroscopic analyzer, said analyzer including a laser capable of vaporizing at least one of the one or more laser vaporizable collection portions of said capture tape and a spectrometer adapted to obtain spectral elements attributable to vaporized collection portions of said capture tape and spectral elements attributable to said collected particle samples;
analyzing in real-time the particle samples collected on the first collection portion by vaporizing at least one of said one or more collection portion with said laser and differentiating between the spectral elements attributable to said vaporized at least one collection portion or said capture tape and spectral elements attributable to sample particles; and
electronically encoding information on the data storage portion related to the sample collection and analysis.

14. The method of claim 13, further comprising the step of:
collecting samples from the particle-laden stream on an additional one of the one or more laser vaporizable collection portions of the sample capture tape at a time nearly simultaneous with the sample collecting on the first portion; and
preserving the samples collected on said additional collection portion.

15. The method of claim 13, wherein the preserving step further comprises:
covering with a sterile tape the samples collected on said additional collection portion.

16. The method of claim 13, further comprising the step of:
pre-concentrating a fluid to be analyzed to form the aerosol stream.

17. The method of claim 13, wherein:
the source of sample capture tape further comprises a source reel; and
the advancing step further comprises indexing the sample capture tape between the source reel and a take up reel.

18. The method of claim 13, wherein the advancing step allows the collection process to continue in an uninterrupted fashion even as the tape is in the act of advancing.

19. The method of claim 13, wherein the one or more collection portions are comprised of a porous filter material.

20. The method of claim 13, further comprising the step of:
providing an alarm upon the detection of an aerosolized agent.

21. The detector of claim 1, wherein the one or more sample collection portions are comprised of adhesive coated materials.

22. The detector of claim 1, wherein the one or more sample collection portions are comprised of a material having a surface incorporating microscopic features designed to capture particles impinged thereupon.

23. The detector of claim 1, wherein the sample dispenser further comprises:
a rotating pulley including two side walls and a cylindrical wall defining an enclosed volume, said dispenser exit port comprising one of a plurality of ports in said cylindrical wall;

an arcuate sealing surface disposed adjacent the rotating pulley so as to seal one or more of the plurality of ports in said cylindrical wall over a portion of a revolution of said rotating pulley;

wherein said sample collection portion of said sample capture tape traverses a section of said pulley cylindrical wall, said sample input port delivers said fluid samples to the enclosed volume of said rotating pulley, and said fluid samples impinge upon said sample collection portion of said capture tape through said dispenser exit pot in said pulley cylindrical wall.

* * * * *